(12) United States Patent
Sutton

(10) Patent No.: US 6,264,640 B1
(45) Date of Patent: Jul. 24, 2001

(54) CATAMENITAL DEVICE

(75) Inventor: Wanda Sutton, 7 Brookside Ave - #2, New Brunswick, NJ (US) 08901

(73) Assignee: Wanda Sutton, New Brunswick, NJ (US)

( * ) Notice: Subject to any disclaimer, the term of this patent is extended or adjusted under 35 U.S.C. 154(b) by 0 days.

(21) Appl. No.: 09/235,684

(22) Filed: Jan. 22, 1999

(51) Int. Cl.[7] .............................. A61F 13/15; A61F 13/20
(52) U.S. Cl. ............. 604/385.18; 604/358; 604/85.17; 604/904; 53/148; 206/363
(58) Field of Search ......................... 604/328, 366, 604/358, 330, 11, 904, 385.17, 685.18; 531/148; 206/363

(56) References Cited

U.S. PATENT DOCUMENTS

| | | | |
|---|---|---|---|
| 3,675,654 | 7/1972 | Baker et al. | 128/287 |
| 3,749,094 | 7/1973 | Duncan | 128/285 |
| 3,762,413 | 10/1973 | Hanke | 128/285 |
| 3,818,912 | 6/1974 | Etz | 128/285 |
| 3,863,636 * | 2/1975 | Johnson | 128/285 |
| 4,548,603 | 10/1985 | Ichijo | 604/385 |
| 4,623,340 | 11/1986 | Luceri | 604/385 |
| 4,673,403 | 6/1987 | Lassen et al. | 604/385 |
| 4,690,679 | 9/1987 | Mattingly et al. | 604/383 |
| 5,346,468 | 9/1994 | Campion et al. | 604/13 |
| 5,458,589 | 10/1995 | Comin-DuMong | 604/358 |
| 5,503,076 | 4/1996 | Yeo | 101/483 |
| 5,769,813 | 6/1998 | Peiler et al. | 604/11 |

* cited by examiner

Primary Examiner—Aaron J. Lewis
Assistant Examiner—Michele Kidwell
(74) Attorney, Agent, or Firm—Mathews, Collins, Shepherd & Gould, P.A.

(57) ABSTRACT

A catamenial device having a portion which faces and/or contacts the garment worn by the user wherein the catamenial device is colored to match the color of the garment worn directly over the device by the user of the device.

1 Claim, 6 Drawing Sheets

CATAMENITAL DEVICE

The present invention relates to improved catamenial devices, particularly catamenial tampons and sanitary napkins wherein the portion of the catamenial device which faces and/or contacts the garment worn by the user is colored to match the color of the garment worn directly over the device by the user of the device.

BACKGROUND OF THE INVENTION

Catamenial devices are well known in the art and include sanitary napkins, of which there are many varieties such as but not limited to panty liners, maxipads, minipads and the like, and tampons. Typically, sanitary napkins are oriented substantially outside the body of the user whereas tampons are oriented substantially inside the body of the user. In every case, however, a portion of the catamenial device remains outside the body of the user and subsequently contacts the garment worn directly over the catamenial device. In the case of tampons, typically a withdrawal means such as a string remains outside the body of the user.

Catamenial tampons including a withdrawal string are well known in the art. Typically, a withdrawal string is attached to one end of the tampon to facilitate removal of the tampon after use. Most of the efforts in developing improvements in tampon withdrawal strings have been directed toward methods for the storage of the withdrawal string. For example, U.S. Pat. No. 2,587,515 discloses a withdrawal string formed in a coil compacted against the tampon base. U.S. Pat. No. 3,135,262 discloses a withdrawal string disposed within the protective wrapper to be used as a tear string for opening the wrapper. U.S. Pat. Nos. 3,477,102 and 3,818,912 disclose a withdrawal string spirally wound and seated in an annular recess formed in the end of the tampon. U.S. Pat. No. 3,863,636 discloses a tampon wherein the main portion of the withdrawal string attached to the tampon base is folded and packed inside a longitudinal bore extending into the tampon and only a small length of the string remains outside the tampon. Each of these improvements are directed toward eliminating the packaging and handling problems presented by the presence of the withdrawal string. U.S. Pat. No. 5,458,589 discloses an improved non-wicking withdrawal string for a tampon.

Sanitary napkins likewise have a portion contacting or facing the garment of the user. The prior art shows several efforts to make the garment-facing side of the napkin such as U.S. Pat. No. 4,548,603, incorporated herein by reference, which discloses providing the garment-facing side of the napkin with a pleasant "soft" color or image pattern to relieve the wearer from unpleasant feelings after use or at the time of disposal. U.S. Pat. No. 4,690,679, incorporated herein by reference, discloses providing color to the side of the sanitary napkin facing the body. U.S. Pat. No. 5,503,076, incorporated herein by reference, discloses providing a colored printed layer between laminated layers to provide the color to a design in an overall laminate suitable for avoiding abrasion to the design in the absorbent device.

However, none of these prior art devices address the problem faced by catamenial device users who have occasion to wear close-fitting garments, namely, that the garment-facing or contacting portion of the catamenial device is easily noticeable through close fitting garments such as bathing suits, bikini bottoms and the like because the garment-facing or contacting portion, typically white or some other noticeable color, necessarily protrudes from the body and usually contrasts with the color of the garment. In fact, the prior art, namely U.S. Pat. No. 3,863,636, teaches that it is desirable to have a withdrawal string that is a different color than the tampon to provide sufficient contrast for easy detection by the user. This problem is of particular concern for women whose profession calls for the wearing of such garments such as models, exotic dancers, lifeguards and the like.

It is therefore an object of the present invention to provide an improved catamenial device wherein the garment-facing or contacting portion of the device such as a withdrawal string of a tampon or the garment-facing side of a sanitary napkin is not noticeable when a user is wearing close-fitting garments.

It is another object of the invention to provide a plurality of catamenial devices, such as but not limited to a package of said devices, each device having a garment-facing or contacting portion of a different color so that a user can select a device having a garment-facing or contacting portion that will match the color of the close-fitting garment to be worn.

SUMMARY OF THE INVENTION

Accordingly, the present invention comprises an apparatus in the form of an improved catamenial device having a garment-facing or contacting portion colored to match the color of a close-fitting garment worn by a catamenial device user.

The apparatus or improved catamenial device comprises a catamenial device of any known construction such as but not limited to the construction set forth in U.S. Pat. No. 3,749,094 to Duncan or U.S. Pat. No. 4,136,699 to Collins et al., both of which are incorporated herein by reference. Where the device of the present invention comprises a tampon said device may or may not be constructed with and/or used in conjunction with a tampon applicator as is commonly known in the art. The tampon further comprises at least one withdrawal string or thread attached to at least one end of the tampon. The withdrawal string is colored so that it can match or substantially match the color of closely-fitting garments worn by a tampon user. The present invention further comprises an embodiment wherein the catamenial device is a tampon having a clear withdrawal string. Where the device of the present invention is a sanitary napkin, the garment-facing or contacting portion of the napkin is colored to substantially match the color of a close-fitting garment worn by the user. In a preferred embodiment a plurality of devices each having a different colored garment-facing or contacting portion is provided so that a selection of colors are available to a catamenial device user to match the garment worn by the user over the device.

BRIEF DESCRIPTION OF THE DRAWINGS

Other objects and advantages of this invention may be seen from the following description when viewed in conjunction with the accompanying drawings wherein.

DESCRIPTION OF THE PREFERRED EMBODIMENT

Figure 1:
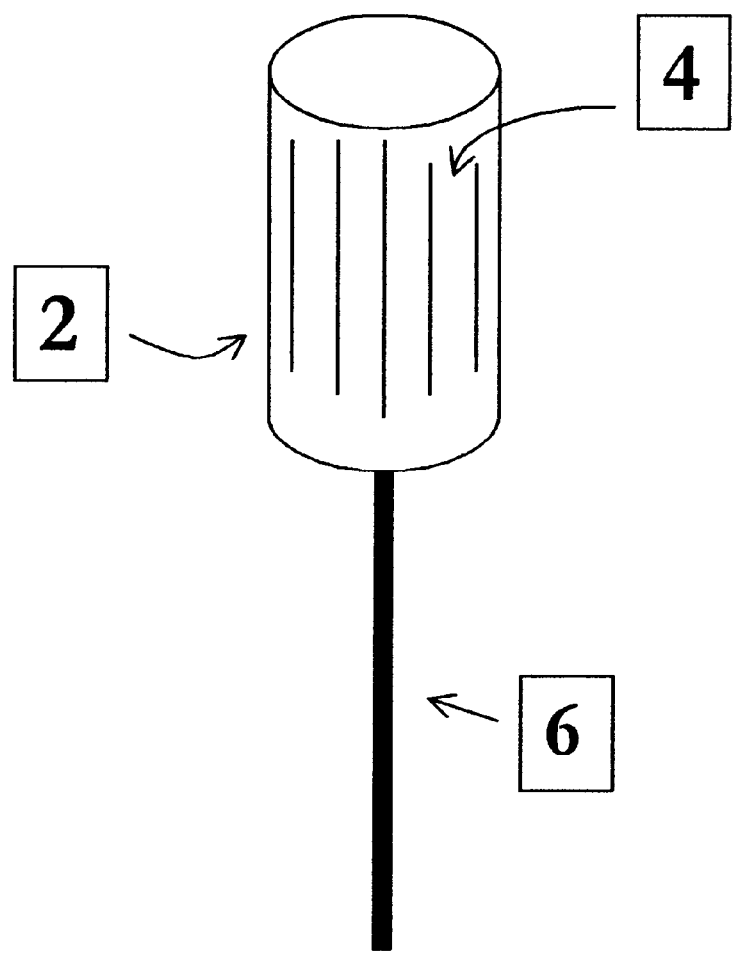
FIG. 1 is a perspective view of one embodiment of the improved catamenial device of the present invention.
Figure 2:
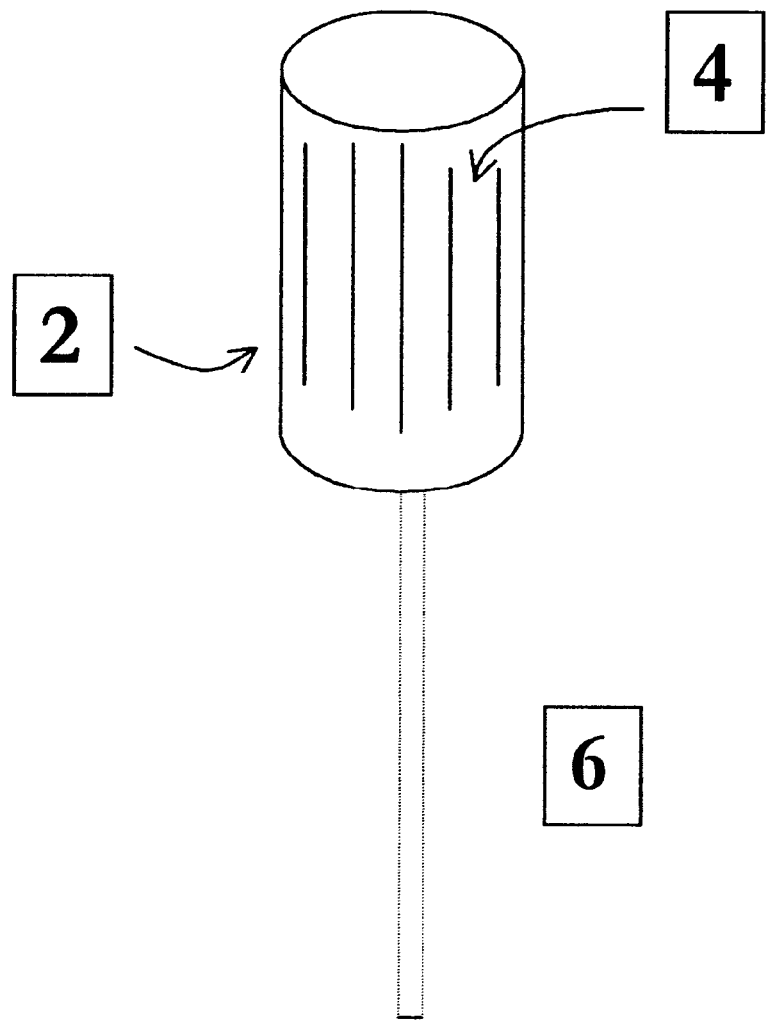
FIG. 2 is a perspective view of a preferred embodiment of the improved catamenial device of the present invention.

As best seen in FIG. 1 an embodiment of the improved catamenial device 2 is a tampon comprised primarily of a tampon or pledget 4 attached to a withdrawal string 6. The pledget 4 typically is comprised of a body of flexible, resilient, elastic, absorbent material. Withdrawal string 6 is attached to at least one end of pledget 4. Withdrawal string 6 is colored to match the color of the garment worn by the user of the tampon so that the withdrawal string 6, necessarily remaining outside the body after insertion of the pledget 4 into the body, is not noticeable through the garment of the tampon user. FIG. 1 indicates a black withdrawal string 6 however string 6 may be any color. The withdrawal string 6 may comprise a string, a loop, a cord, a thread, a tape, a filament or any other means attached to said pledget 4 which may be used for withdrawing the pledget 4 after use. Now referring to FIG. 2, the withdrawal string 6 may further be colorless, transparent, clear or otherwise not readily visible, such as but not limited to a tape or filament, for applications where the garment of the user is particularly sheer or transparent.

Any number of known methods for coloring the withdrawal string 6 may be employed, however, it is preferred that the colored string be colorfast.

Figure 3:
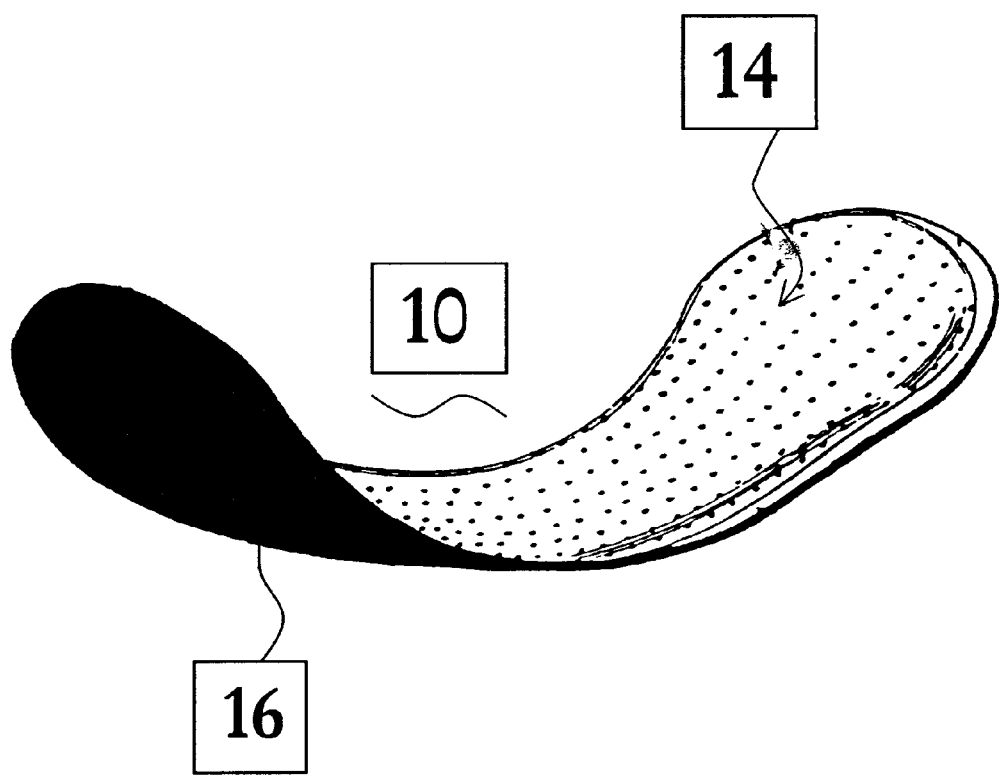
FIG. 3 is a perspective view of another embodiment of the improved catamenial device of the present invention.

Now referring to FIG. 3, in another embodiment the present invention comprises a sanitary napkin 10 comprised of an absorbent pad 12 typically comprised of an absorbent core (not shown), a body-facing side comprised of a cover member 14 of known composition such as but not limited to that disclosed in U.S. Pat. No. 4,673,403, incorporated herein by reference, and a garment-facing side 16 which is comprised of a fluid-impervious shield typically incorporated in a sanitary napkin. The garment-facing side may be comprised of a polymeric film or nonwoven material bearing a polymeric film. The garment-facing side 16 is colored to match the color of the garment worn directly over the sanitary napkin by the user. FIG. 3 indicates a black garment-facing side, however, any color may be employed. The sanitary napkin 10 may further comprise adhesive strips or tabs (not shown) for securing the napkin 10 to the undergarment of the user, in which case the adhesive strips or tabs are the same color as the garment-facing side 16 of the napkin 10.

Any known method for coloring the garment-facing or contacting portion of the catamenial device of the present invention side may be employed, such as but not limited to spraying, soaking, silk screening and the like. Any suitable ink or dye may be employed. Suitable dyes or inks are permanent, so as not to stain the wearer or the garments of the wearer, and nontoxic and nonirritating to the wearer. Suitable dyes include but are not limited to dyes such as FLEXO 910 light blue ink No. 85NK395 from Fremond Inks. In this respect the present invention represents an improvement in that the improved catamenial devices avoid the need for a user to attempt to color the garment-facing or contacting portion themselves. Now referring to FIG. 5 the devices of the present invention ideally are sterile and packaged individually in transparent wrappers 12 to maintain sterility until use and enabling a user to select a device having the desired color. Alternatively, now referring to FIG. 6, the devices may be packaged in opaque wrappers 14 with color identifying indicia 16 on the wrapper. Indicia 16 may comprise a word description, color or the like to identify the color of the device.

Figure 4:
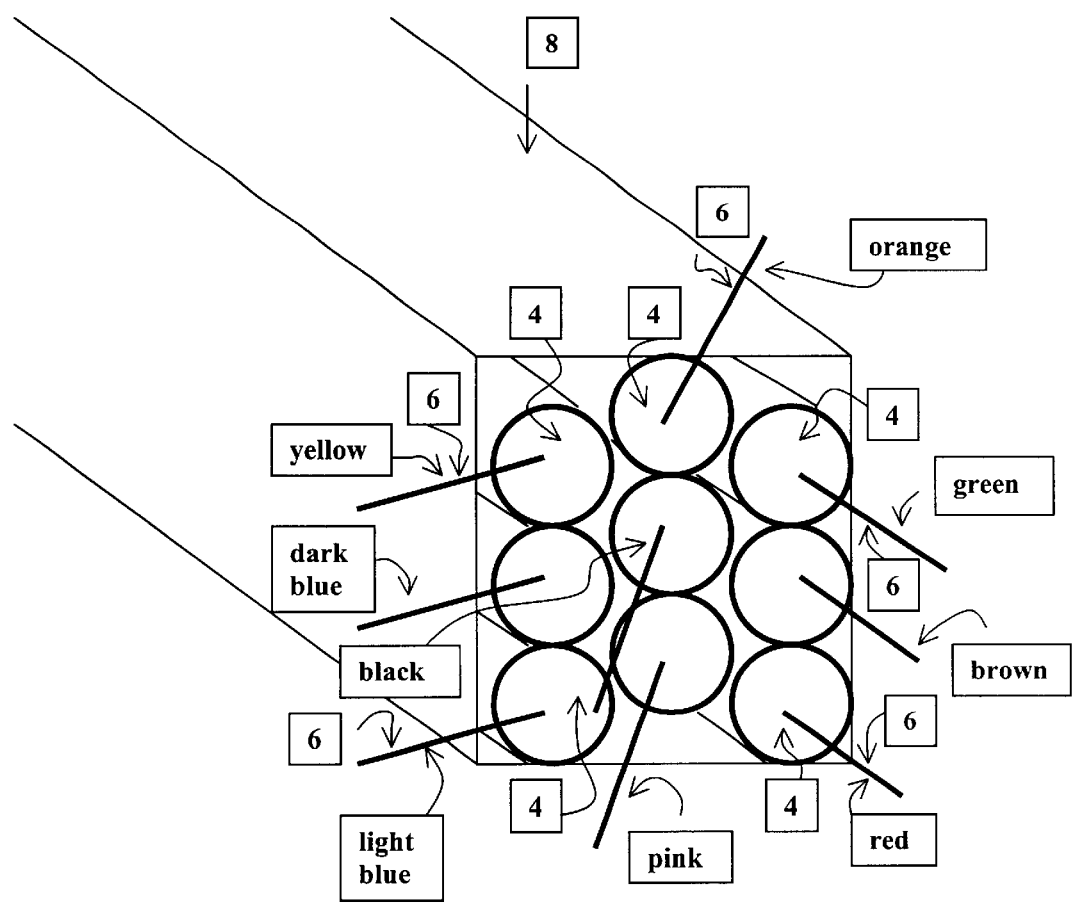
FIG. 4 is a perspective view of another preferred embodiment of the present invention.

Now referring to FIG. 4, in a preferred embodiment, a plurality of catamenial tampons 2 are provided in a package 8 wherein the color of the withdrawal string 6 is different for each tampon 2. In another embodiment (not shown) a plurality of tampons 2 are provided in a package wherein the color of the withdrawal string 6 is the same for some of the tampons 2 and different for other of the tampons 2. Tampons 2 are preferably individually wrapped in clear or color-indicating wrappers.

Figure 5:
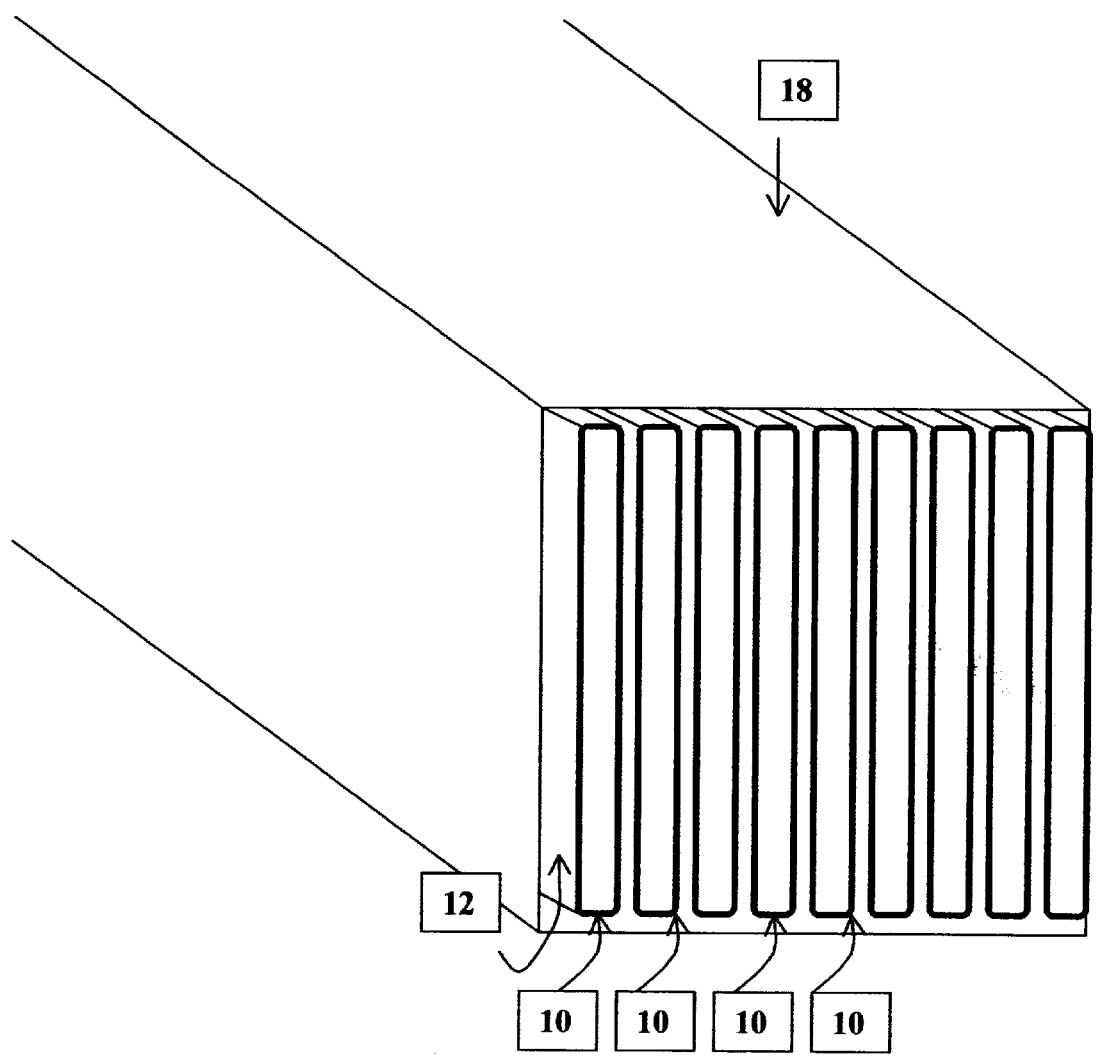
FIG. 5 is a perspective view of another preferred embodiment of the present invention.
Figure 6:
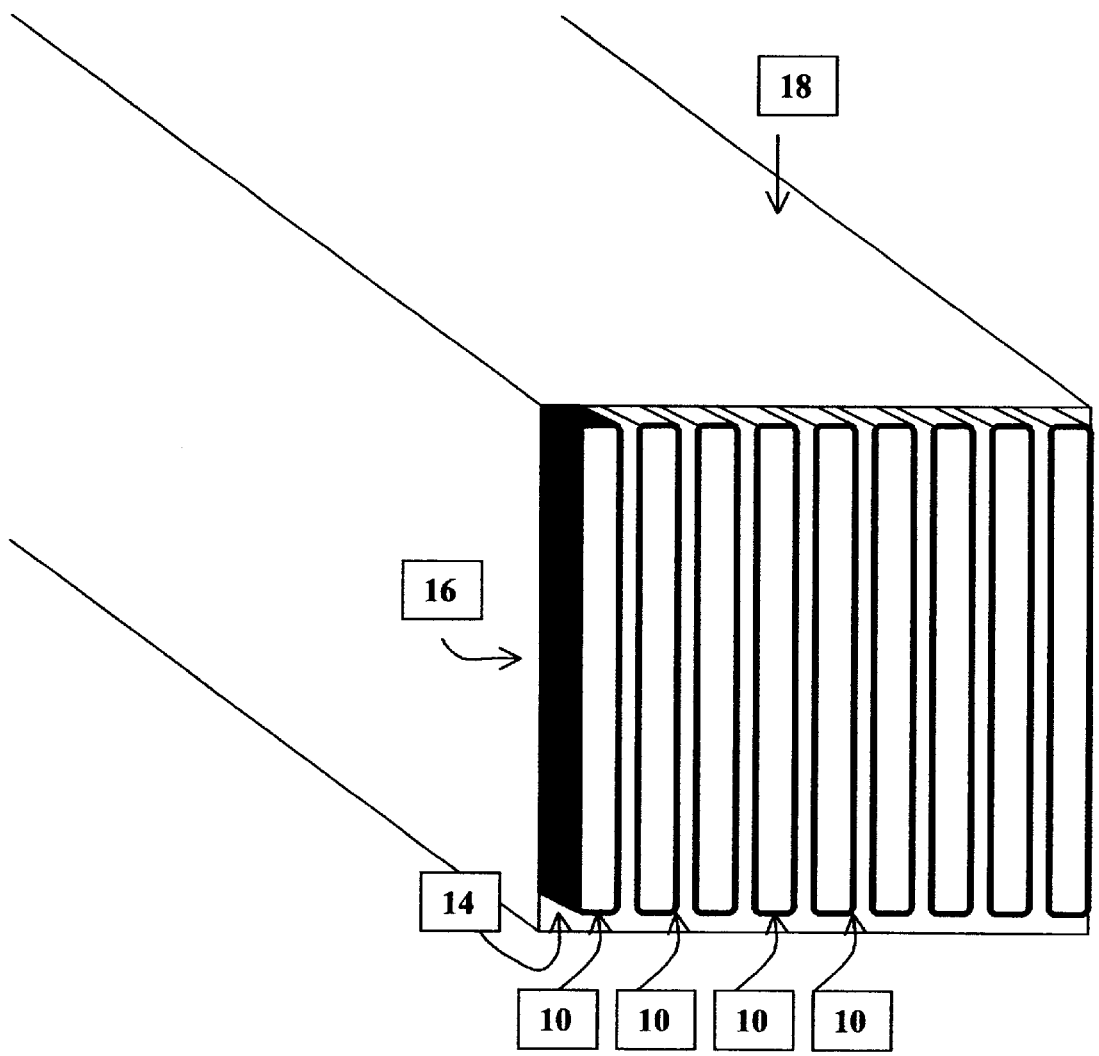
FIG. 6 is a perspective view of another preferred embodiment of the present invention.

Now referring to FIG. 5, in another preferred embodiment, a plurality of sanitary napkins 10 are provided in a package 18 wherein the color of the garment-facing side 16 is different for each napkin 10. In another embodiment (not shown) a plurality of sanitary napkins are provided in a package wherein the color of the garment-facing side 16 is the same for some of the napkins 10 and different for other of the napkins 10. Napkins 10 are preferably individually wrapped in clear or color-indicating wrappers 12.

Various modifications to the above invention will become apparent to those skilled in the art, all of which are intended to fall within the spirit and scope of the present invention, limited only by the appended claims. All patents and publications referred to herein are hereby incorporated by reference.

What is claimed is:

1. A package comprising a plurality of catamenial tampons each of said tampons comprising a pledget and colored withdrawal means wherein the color of the withdrawal means is different for each of said tampons.

\* \* \* \* \*